(12) United States Patent
Gwag et al.

(10) Patent No.: US 7,608,585 B2
(45) Date of Patent: Oct. 27, 2009

(54) COMPOSITIONS FOR INHIBITION OF NECROSIS INDUCED BY A NEUROTROPHIN

(75) Inventors: Byoung Joo Gwag, Suwon-si (KR); Sung-Hwa Yoon, Suwon-si (KR); Sun-Hee Kim, Suwon-si (KR); Seok-Joon Won, Suwon-si (KR)

(73) Assignee: Neurotech Pharmaceuticals Co., Ltd., Suwon-si (KR)

( * ) Notice: Subject to any disclaimer, the term of this patent is extended or adjusted under 35 U.S.C. 154(b) by 385 days.

(21) Appl. No.: 10/542,936

(22) PCT Filed: Jan. 20, 2004

(86) PCT No.: PCT/KR2004/000119

§ 371 (c)(1),
(2), (4) Date: Jul. 19, 2005

(87) PCT Pub. No.: WO2004/064844

PCT Pub. Date: Aug. 5, 2004

(65) Prior Publication Data

US 2006/0135600 A1    Jun. 22, 2006

(51) Int. Cl.
   *A61K 38/18*   (2006.01)
   *C07C 229/68*  (2006.01)
   *C07K 14/475*  (2006.01)

(52) U.S. Cl. .................. 514/12; 562/453; 530/399
(58) Field of Classification Search ............... None
   See application file for complete search history.

(56) References Cited

U.S. PATENT DOCUMENTS 5,762,922 A   6/1998   Noble et al. ............... 424/85.4

FOREIGN PATENT DOCUMENTS

WO   WO 95/22342   8/1995
WO   WO 01/79153   10/2001

OTHER PUBLICATIONS

Iacovitti 1999. Brain Research 816:276-285.*
Mattson, M.P. et al., "Mechanisms of Neurotrophic Factor Protection against Calsium- and Free Radical-Mediated Excitotoxic Injury: Implication for Treating Neurodegenerative Disorders," *Experimental Neurology* 124(1):89-95, 1993.
Yaqub, B.A., "New Horizons in management of Alzheimer's disease," *Saudi Medical Journal* 20(9): 671-677, 1999.
Alcántara, S. et al., "TrkB Signaling Is Required for Postnatal Survival of CNS Neurons and Protects Hippocampal and Motor Neurons from Axotomy-Induced Cell Death," *The Journal of Neuroscience* 17(10): 3623-3633, May 15, 1997.
Apfel, S.C., "Neurotrophic Factor Therapy—Prospects and Problems," *Clinical Chemistry and Laboratory Medicine* 39(4): 351-355 2001.
Bates, B. et al., "Neurotrophin-3 Promotes Cell Death Induced in Cerebral Ischemia, Oxygen-Glucose Deprivation, and Oxidative Stress: Possible Involvement of Oxygen Free Radicals," *Neurobiology of Disease* 9: 24-37, 2002.
Borasio, G.D. et al., "Involvement of ras p21 in Neurotrophin-induced Response of Sensory by Not Sympathetic Neurons," *The Journal of Cell Biology* 121(3): 665-672, May 1993.
Bowling, A.C. et al., "Superoxide Dismutase Activity, Oxidative Damage, and Mitochondrial Energy Metabolism in Familial and Sporadic Amyotophic Lateral Sclerosis," *Journal of Neurochemistry* 61(6): 2322-2325, Dec. 1993.
Bradford, H.F. et al., "Neurotrophins in the Pathogenesis and Potential Treatment of Parkinson's Disease," *Advances in Neurology* 80: 19-25, 1999.
Brown S.A. et al., "Role of oxygen-derived free radicals in the pathogenesis of shock and trauma, with focus on central nervous system injuries," *Journal of the American Veterinary Medical Association* 200(12): 1849-1859, Jun. 15, 1992.
Deshmukh, M. et al., "Programmed Cell Death in Neurons: Focus on the Pathway of Nerve Growth Factor Deprivation-Induced Death of Sympathetic Neurons," *Molecular Pharmacology* 51: 897-906, 1997.
Fernández-Sánchez, M.T. et al., "Basic fibroblast growth factor protects cerebellar neurons in primary culture from NMDA and non-NMDA receptor mediated neurotoxicity," *FEBS Letters* 335(1): 124-131, Nov. 1993.
Ferrer, I. et al., "Brain-derived neurotophic factor reduces cortical cell death by ischemia after middle cerebral artery occlusion in the rat," *Neuropathologica* 101(3): 229-238, 2001.
Friedman, B. et al., "BDNF and NT-4/5 Exert Neurotrophic Influences on Injured Adult Spinal Motor Neurons," *The Journal of Neuroscience* 15(2): 1044-1056, Feb. 1995.
Frim, D.M. et al., "Implanted fibroblasts genetically engineered to produce brain-derived neurotrophic factor prevent 1-methy-4-phenylpyridinium toxicity to dopaminergic neurons in the rat," *Proc. Natl. Acad. Sci. USA* 91: 5104-5108, May 1994.
Gash, D.M. et al., "Functional recovery in parkinsonian monkeys treated with GDNF," *Nature* 380: 252-255, Mar. 21, 1996.
Gwag, B.J. et al., "BDNF or IGF-1 potentiates free radical-mediated injury in cortical cell cultures," *Neuroreport* 7: 93-96, 1995.
Hall, E.D. et al., "Nonsteroidal Lazaroid U7851F in Models of Focal and Global Ischemia," *Stroke* 21(11 Suppl. III): III83-III87, Nov. 1990.
He, Y. et al., "6-Hydroxydopamine induced apoptosis of dopaminergic cells in the rat substantia nigra," *Brain Research* 858: 163-166, Mar. 2000.

(Continued)

*Primary Examiner*—Robert C Hayes
(74) *Attorney, Agent, or Firm*—Seed IP Law Group PLLC

(57) ABSTRACT

Disclosed is a method for inhibition of necrosis induced by neurotrophin, and more specifically a method for inhibition of necrosis by administrating oxidative stress inhibitor and a method for simultaneous inhibition of necrosis and apoptosis by administrating oxidative stress inhibitor and neurotrophin. The oxidative stress inhibitor of the present invention can inhibit nerve cell necrosis induced by neurotrophin. Moreover, it can be used for protecting nerve cell damage connected with alzheimer disease, parkinson's disease, degenerating cerebropathia and promoting regeneration of the nerve cells by administrating oxidative stress inhibitor and neurotrophin.

2 Claims, 9 Drawing Sheets

OTHER PUBLICATIONS

Hefti, F., "Nerve Growth Factor Promotes Survival of Septal Cholinergic Neurons After Fimbrial Transections," *The Journal of Neuroscience* 6(8): 2155-2162, Aug. 1986.

Hetman, M. et al., "Neuroprotection by Brain-derived Neurotrophic Factor Is Mediated by Extracellular Sing-regulated Kinase and Phosphatidylinositol 3-Kinase," *The Journal of Biological Chemistry* 274(32): 22569-22580, Aug. 6, 1999.

Holtzman, D.M. et al., "Nerve Growth Factor Protects the Neonatal Brain Against Hypoxic—Ischemic Injury," *Annals of Neurology* 39(1): 114-122, Jan. 1996.

Hwang, J.-J. et al., "The role of NADPH oxidase, neuronal nitric oxide synthase and poly(ADP ribose) polymerase in oxidative neuronal death induced in cortical cultures by brain-derived neurotrophic factor and neurotrophin-4/5," *Journal of Neurochemistry* 82: 894-902, 2002.

Jin, Y. et al., "Transplants of Fibroblasts Genetically Modified to Express BDNF Promote Axonal Regeneration from Supraspinal Neurons Following Chronic Spinal Cord Injury," *Experimental Neurology* 177: 265-275, 2002.

Juurlink, B.H.J. et al., "Review of Oxidative Stress in Brain and Spinal Cord Injury: Suggestions for Pharmacological and Nutritional Management Strategies," *Journal of Spinal Cord Medicine* 21(4): 309-334, Oct. 1998.

Kim, S.H. et al., "Brain-derived neurotrophic factor can act as a pronecrotic factor through transcriptional and translational activation of NADPH oxidase," *The Journal of Cellular Biology* 159(5): 821-831, Dec. 9, 2002.

Ko, M-L. et al., "The Combined Effect of Brain-Derived Neurotrophic Factor and a Free Radical Scavenger in Experimental Glaucoma," *Investigative Ophthalmology & Visual Science* 41(10): 2967-2971, Sep. 2000.

Koh, J-Y. et al., "Potentiated Necrosis of Cultured Cortical Neurons by Neurotrophins," *Science* 268: 573-575, Apr. 28, 1995.

Levi-Montalcini, R., "The Nerve Growth Factor: thirty-five years later," *The EMBO Journal* 6(5): 1145-1154, 1987.

Levivier, M. et al., "Intrastriatal Implantation of Fibroblasts Genetically Engineered to Produced Brain-Derived Neurotrophic Factor Prevents Degeneration of Dopaminergic Neurons in a Rat Model of Parkinson's Disease," *The Journal of Neuroscience* 15(12): 7810-7820, Dec. 1995.

Lewis, G.P. et al., "Effects of the Neurotrophic Brain-Derived Neurotrophic Factor in an Experimental Model of Retinal Detachment," *Investigative Ophthalmology & Visual Science* 40(7): 1530-1544, Jun. 1999.

Lobner, D. et al., "Neutrotrophic Factor Effects on Oxidative Stress—Induced Neuronal Death," *Neurochemical Research* 28(5): 749-756, May 2003.

Louvel, E. et al., "Therapeutic advances in amyotrophic lateral sclerosis," *Trends in Pharmacological Sciences* 18: 196-203, Jun. 1997.

Lovell, M.A. et al., "Copper, iron and zinc in Alzheimer's disease senile plaques," *Journal of the Neurological Sciences* 158: 47-52, 1998.

Montine, T.J. et al., "Crosslinking of Apolipoprotein E by Products of Lipid Peroxidation," *Journal of Neuropathology and Experimental Neurology* 55: 202-210, Feb. 1996.

Morse, J. K. et al., "Brain-derived Neurotrophic Factor (BDNF) Prevents the Degeneration of Medial Septal Cholinergic Neurons Following Fimbria Transection," *The Journal of Neuroscience* 13(10): 4146-4156, Oct. 1993.

Olson, L., "Toward trophic treatment in parkinsonism: A primate step," *Nature Medicine* 2(4): 400-401, Apr. 1996.

Pérez-Navarro, E. et al., "Brain-Derived Neurotrophic Factor, Neurotrophin-3, and Neurotrophin-4/5 Prevent the Death of Striatal Projection Neurons in a Rodent Model of Huntingtons's Disease," *Journal of Neurochemistry* 75(5): 2190-2199, 2000.

Samdani, A.F. et al., "Differential Susceptibility to Neurotoxicity Mediated by Neurotrophins and Neuronal Nitric Oxide Synthase," *The Journal of Neuroscience* 17(12): 4633-4641, Jun. 15, 1997.

Siegel, G.J. et al., "Neurotrophic factors in Alzheimer's and Parkinson's disease brain," *Brain Research Reviews* 33(2-3): 199-227, Sep. 2000.

Smith, M.A. et al, "Oxidative Posttranslational Modifications in Alzheimer Disease. A Possible Pathogenic Role in the Formation of Senile Plaques and Neurofibrillary Tangles," *Molecular And Chemical Neuropathology* 28(1-3): 41-48, May-Aug. 1996.

Smith, M.A. et al., "Iron accumulation in Alzheimer disease is a source of redox-generated free radicals," *Proc. Natl. Acad. Sci. USA* 94: 9866-9868, Sep. 1997.

Smith, M.A. et al., "Radical AGEing in Alzheimer's disease," *Trends in Neurosciences* 18(4): 172-176, Apr. 1995.

Springer, J.E. et al., "4-Hydroxynonenal, a Lipid Peroxidation Product, Rapidly Accumulates Following Traumatic Spinal Cord Injury and Inhibits Glutamate Uptake," *Journal of Neurochemistry* 68(6): 2469-2476, 1997.

Tatton, N.A. et al., "In situ detection of apoptotic nuclei in the substantia nigra compacta of 1-methyl-4-phenyl-1,2,3,6=tetrahydropyridine-treated mice using terminal deoxynucleotidyl transferase labeling and acridine orange staining," *Neuroscience* 77(4): 1037-1048, Apr. 1997.

Turmel, H. et al., "Caspase-3 Activation in 1-methyl-4-Phenyl-1,2,3,6-Tetrahydropyridine (MPTP)-Treated Mice," *Movement Disorders* 16(2): 185-189, Mar. 2001.

Vitek, M.P. et al., "Advanced glycation end products contribute to amyloidosis in Alzheimer disease," *Proc. Natl. Acad. Sci. USA* 91: 4766-4770, May. 1994.

Won, S.J. et al., "NT-4/5 Exacerbates Free Radical-Induced Neuronal Necrosis in Vitro and in Vivo," *Neurobiology of Disease* 7: 251-259, 2000.

Yao, R. et al., "Requirement for Phosphatidylinositol-2 Kinase in the Prevention of Apoptosis by Nerve Growth Factor," *Science* 267: 2003-2006, Mar. 31, 1995.

* cited by examiner

COMPOSITIONS FOR INHIBITION OF NECROSIS INDUCED BY A NEUROTROPHIN

TECHNICAL FIELD

The present invention relates to a pharmacological composition for prevention of neuronal necrosis induced by neurotrophins, more particularity, to a method for prevention of neurotrophin-induced neuronal death by anti-oxidants and synergetic effects of neurotrophins and anti-oxidants for enhanced promotion of neuronal survival.

BACKGROUND ART

Survival of central and peripheral neurons largely depends upon contact with neurotrophins that are released from their target cells (Levi-Montalcini, 1987, *EMBO J.*, 6, 1145-1154; Barde, 1994, *Prog. Clin. Biol. Res.*, 390, 45-56). The neurotrophic effect of neurotrophins is initiated through binding to TrkA, TrkB, or TrkC, the high affinity neurotrophin receptors with tyrosine kinase activity (Patapoutian and Reichardt, 2001, *Curr. Opin. Neurobiol.*, 11, 272-280; Kaplan and Miller, 2000, *Curr. Opin. Neurobiol.*, 10, 381-391). The Trk tyrosine kinases activate the small GTP-binding protein Ras, PI-3K, and PLC, which play an important role in survival of a variety of neurons including cerebellar granule, cortical, hippocampal, sympathetic, and sensory neurons (Borasio et al., 1993, *J. Cell Biol.*, 121, 665-672; Stephens et al., 1994, *Neuron*, 12, 691-705; Yao and Cooper, 1995, *Science.*, 267, 2003-2006; Nobes et al., 1996, *Neuroscience.*, 70, 1067-1079; Nonomura et al., 1996, *Brain Res Dev Brain Res.*, 97, 42-50; Alcantara et al., 1997, *J Neurosci.*, 17(10), 3623-3633; Hetman et al., 1999, *J Biol Chem.*, 274, 22569-22580; Atwal et al., 2000, *Neuron.*, 27, 265-227).

Neurotrophins enhance neuronal survival by interfering with programmed cell death or apoptosis in the process of normal development (Barde, 1994, *Prog. Clin. Biol. Res.*, 390, 45-56; Deshmukh and Johnson, 1997, *Mol. Pharmacol.*, 51, 897-906). The neuroprotective effects of neurotrophins have been observed in the central neurons subjected to pathological insults. For example, neurotrophins ameliorate degeneration of basal forebrain cholinergic neurons, retinal ganglion neurons, and spinal sensory and motor neurons following axotomy in vivo (Hefti, 1986, *J. Neurosci.*, 6, 2155-2162; Yan et al., 1993, *J. Neurobiol.*, 24, 1555-1577; Mey and Thanos, 1993, *Brain Res.*, 602, 304-317; Morse et al., 1993, *J. Neurosci.*, 13, 4146-4156; Cohen et al., 1994, *J. Neurobiol.*, 25, 953-959; Friedman et al., 1995, *J. Neurosci.*, 15, 1044-1056). Nerve growth factor (NGF), brain-derived neurotrophic factor (BDNF), and neurotrophins (NT)-4/5 can reduce neuronal death following hypoxic-ischemic injury (Hefti, 1986, *J. Neurosci.*, 6, 2155-2162; Yan et al., 1993, *J. Neurobiol.*, 24, 1555-1577; Mey and Thanos, 1993, *Brain Res.*, 602, 304-317; Morse et al., 1993, *J. Neurosci.*, 13, 4146-4156; Cohen et al., 1994, *J. Neurobiol.*, 25, 953-959; Friedman et al., 1995, *J. Neurosci.*, 15, 1044-1056). BDNF protects dopaminergic neurons from 1-methyl-4-phenyl-1,2,3,6-tetrahydropyridine and 6-hydroxy dopamine (Spina et al., 1992, *J. Neurochem.*, 59, 99-106; Frim et al., 1994, *Proc. Natl. Acad. Sci. U.S.A.*, 91, 5104-5108).

The findings above suggest therapeutic potential of neurotrophins for hypoxic-ischemia and various neurodegenerative diseases. However, the beneficial effects of neurotrophins should be compromised with a notion that neurotrophins can exacerbate certain forms of neuronal injury. BDNF, NT-3, or NT-4/5 renders neurons highly vulnerable to deprivation of oxygen and glucose, possibly by enhancing $Ca^{2+}$ influx and NO (nitric oxide) production through N-methyl-D-aspartate (NMDA) glutamate receptors (Fernandez-Sanchez and Novelli, 1993, *FEBS Lett.*, 335, 124-131; Koh et al., 1995, *Science*, 268, 573-575; Samdani et al., 1997, *J. Neurosci.*, 17, 4633-4641). BDNF, NGF, and NT-4/5 potentiate neuronal cell necrosis induced by oxidative stress or zinc in cortical cell cultures (Gwag et al., 1995, *Neuroreport*, 7, 93-96; Park et al., 1998, *Neuroreport*, 9, 687-690; Won et al., 2000, *Neurobiol Dis*, 7, 251-259).

Recently, the present inventors have found that neurotrophins can directly induce neuronal cell necrosis in cortical cell cultures and adult rats as well as the potentiation effects of certain neuronal injury (Kim et al., 2002, *J. Cell Biol*, 159, 821-831). Accordingly, the unexpected neurotoxicity of neurotrophins likely explains failure of clinical trials in neuropathic pain and amyotrophic lateral sclerosis (Apfel et al., 2001, *Clin. Chem. Lab. Med*, 39(4), 351-61).

Thus, the inventors have delineated mechanisms underlying toxic effects of neurotrophins, investigated drugs for prevention of neurotrophin toxicity, and completed the present invention by developing a method for optimizing therapeutic effects of neurotrophins with anti-oxidants.

DISCLOSURE OF THE INVENTION

The present invention provides a method for preventing neurotrophin-induced neuronal cell necrosis with administration of anti-oxidants, and also provides a method for preventing neuronal apoptosis and necrosis with concurrent administration of neurotrophins and anti-oxidants.

The present invention provides a method for preventing neurotrophin-induced neuronal cell necrosis with administration of anti-oxidants.

The present invention provides a method for preventing neuronal apoptosis and necrosis at the same time with concurrent administration of neurotrophins and anti-oxidants.

The present invention provides a method for preventing neurotrophin-induced neuronal cell necrosis with administration of tetrafluorobenzyl derivatives.

The present invention provides a method for preventing neuronal apoptosis and necrosis with concurrent administration of neurotrophins and tetrafluorobenzyl derivatives.

BRIEF DESCRIPTION OF THE DRAWINGS

The above and other objects, features and other advantages of the present invention will be more clearly understood from the following detailed description taken in conjunction with the accompanying drawings.

A: treatment with BDNF B: treatment with NT-3 C: treatment with NT-4/5

Figure 2:
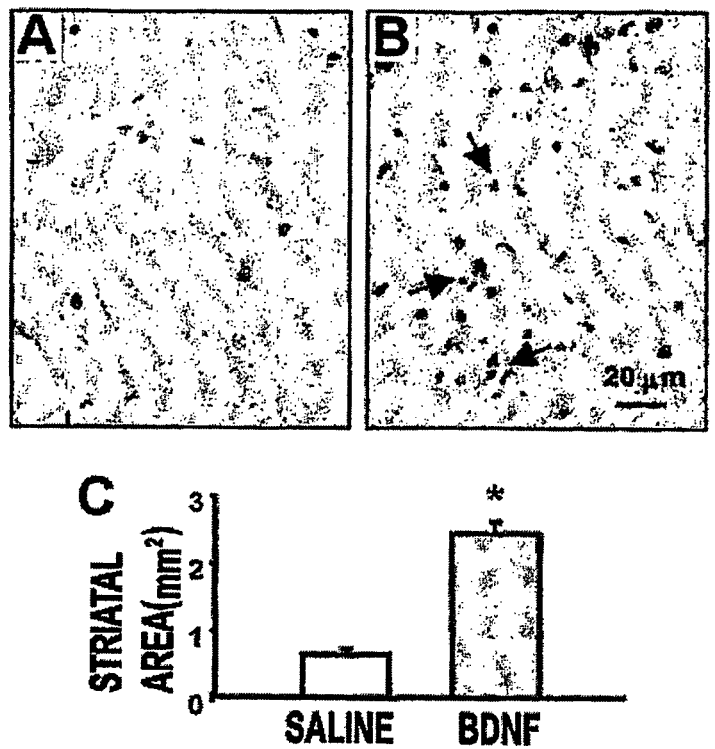

FIG. 2 is graph showing neuronal necrosis in brain sections stained with hematoxylin-eosin (H&E) at 2 day after intrastriatal injections of saline or BDNF.

Figure 3:
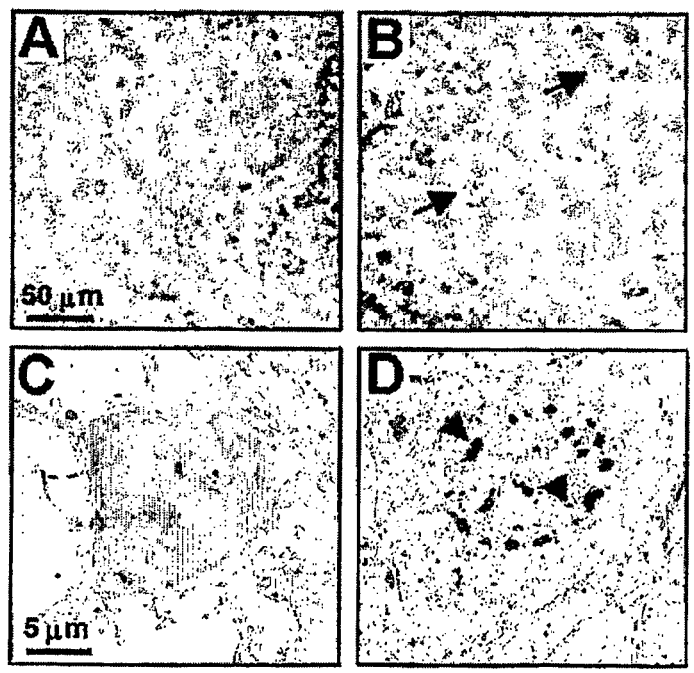
Figure 4:
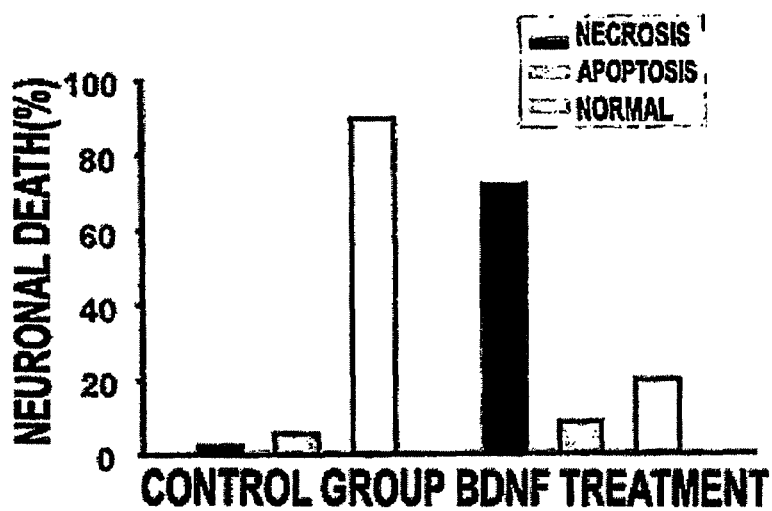

A: Bright field photomicrogrphs of brain sections stained with H&E after intrastriatal injections of saline B: Bright field photomicrogrphs of brain sections stained with H&E after intrastriatal injections of BDNF C: a graph showing quantitative analysis of degenerating neurons in brain sections stained with H&E after injections of saline or BDNF FIG. 3 is a graph showing photomicrograph of cortical neurons 32 hr after a sham wash or exposure to BDNF A: Phase contrast photomicrograph of a sham wash B: Phase contrast photomicrograph of BDNF C: Electron photomicrograph of a sham wash
D: Electron photomicrograph of BDNF FIG. 4 is a graph showing patterns of BDNF-induced neuronal death, degenerating neurons were defined as normal, necrosis (see above), or apoptosis, from sham wash group and control group at 32 hr following exposure of cortical cell cultures to BDNF.

Figure 5:
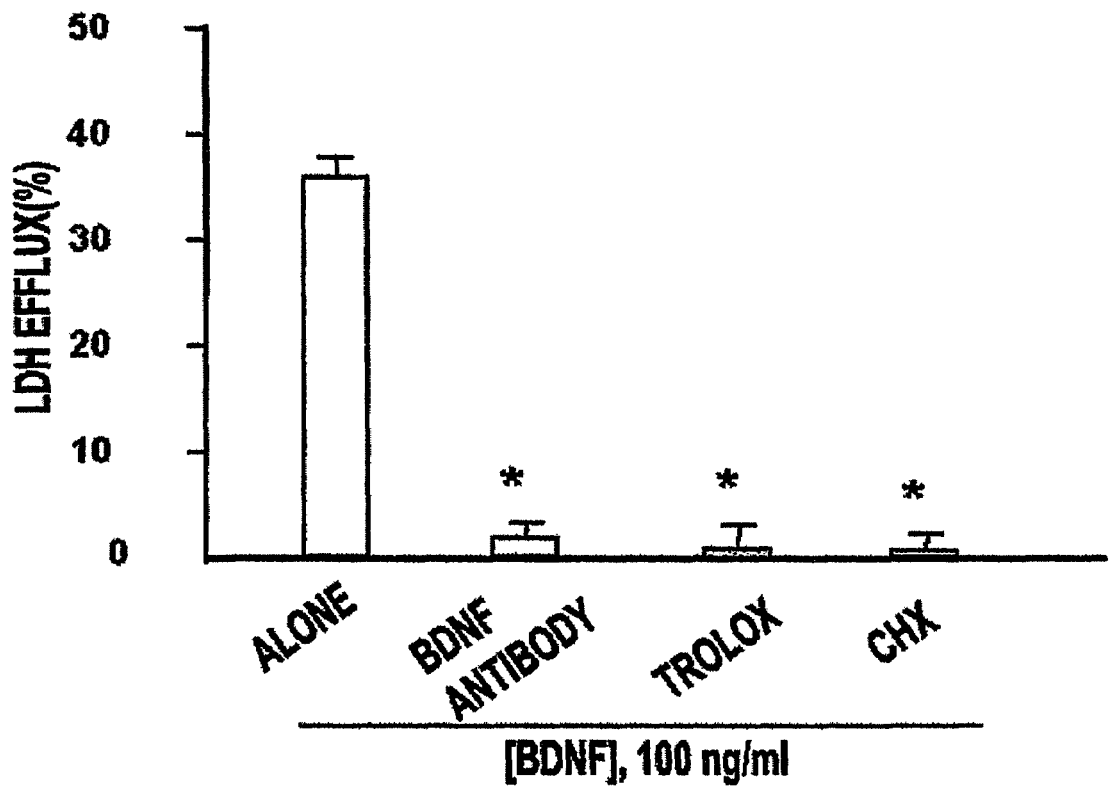

FIG. 5 is a graph showing neuronal death analyzed by measurement of LDH efflux into the bathing medium in cortical neurons after continuous exposure to BDNF, alone or with anti-BDNF blocking antibody, trolox, or CHX (cycloheximide).

Figure 6:
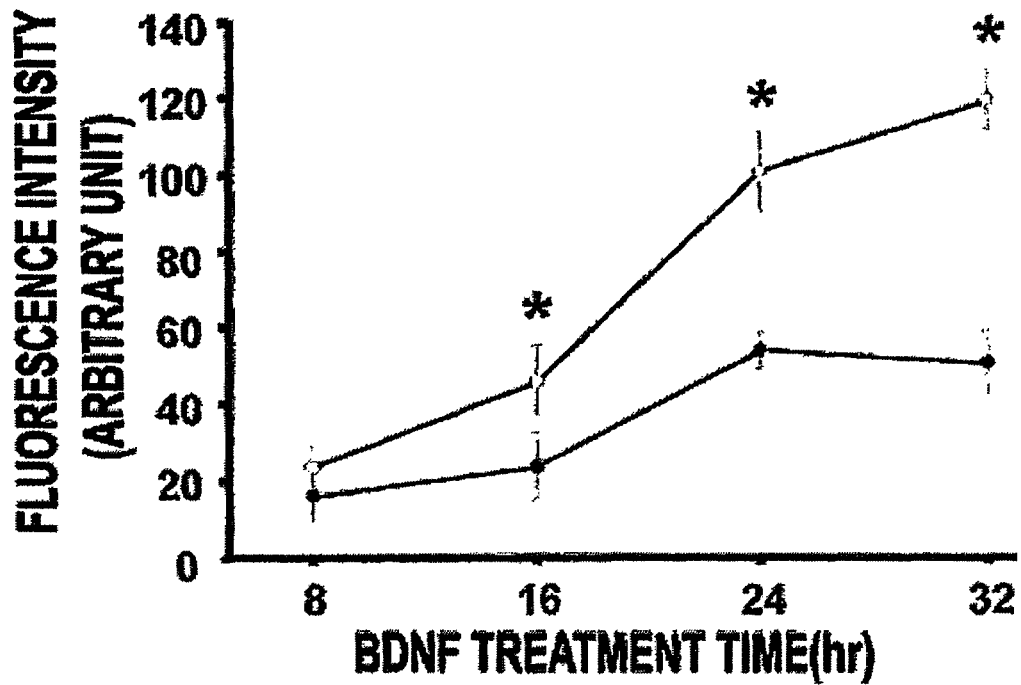

FIG. 6 is a graph showing levels of ROS exposed to a sham wash or BDNF in cortical neurons analyzed at indicated times by measuring fluorescence intensity of oxidized DCDHF-DA (DCF).

Figure 7:
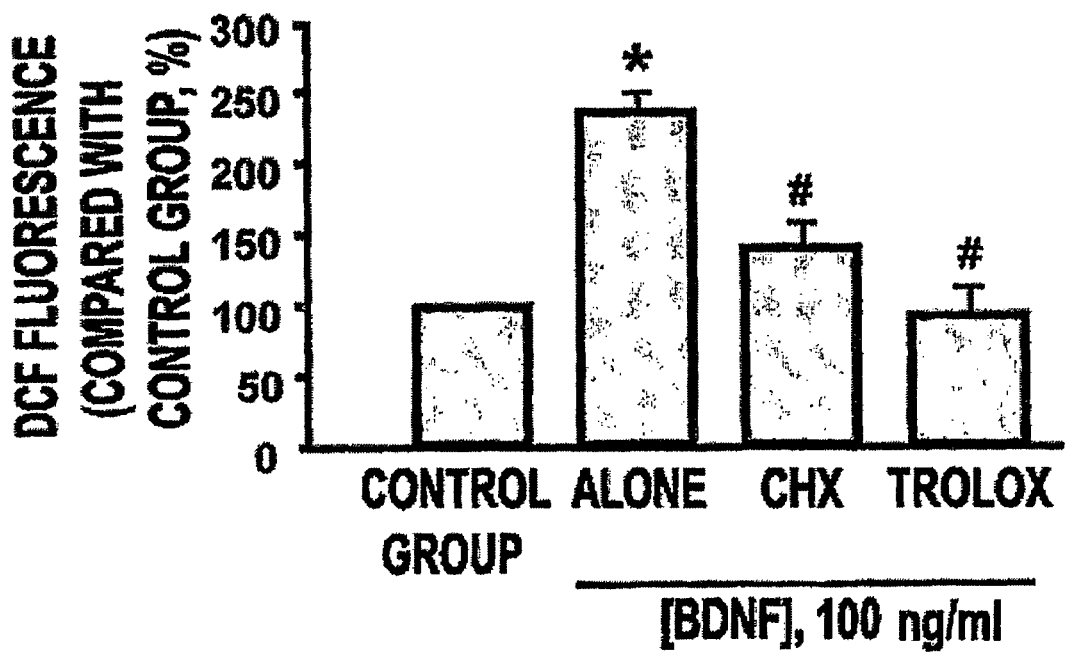

FIG. 7 is a graph showing fluorescence quantitation of DCF in cortical neurons after 32 hr exposure of cortical cell cultures to a sham wash or 100 ng/ml BDNF, alone or in the presence of CHX or trolox.

Figure 8:
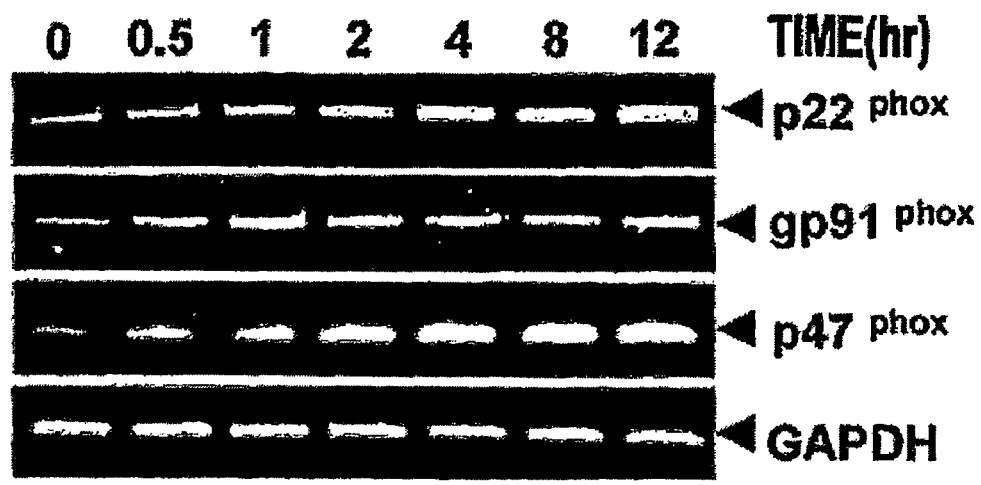

FIG. 8 is a graph showing RT-PCR analysis of NADPH oxidase and GAPDH mRNA expression in cortical cell cultures exposed to BDNF for indicated times.

Figure 9:
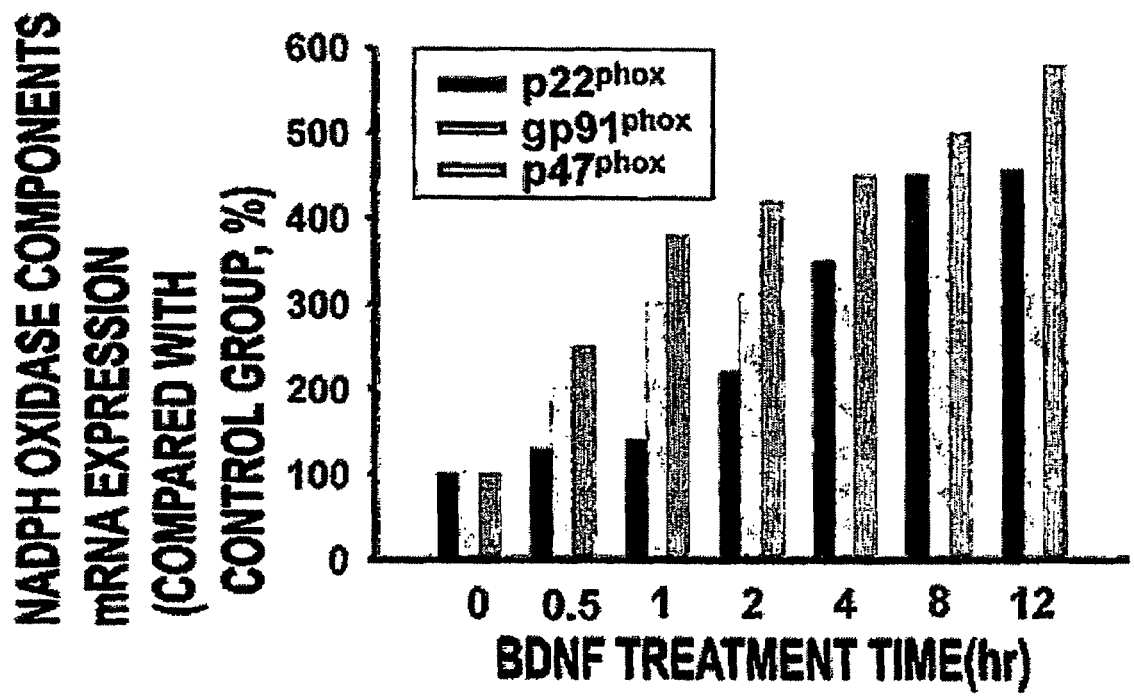

FIG. 9 is a graph quantitatively showing the mRNA level of NADPH oxidase and GAPDH mRNA expression in cortical cell cultures exposed to BDNF for indicated times.

Figure 10:
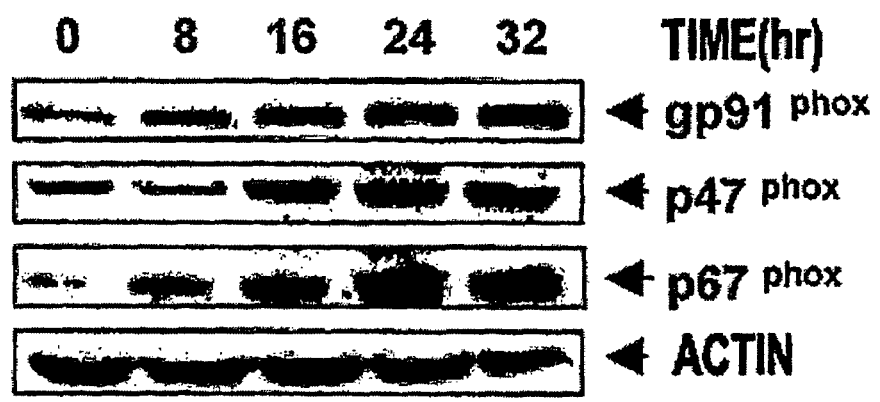

FIG. 10 is a graph showing western blot analysis of NADPH oxidase and actin expression in cortical cell cultures following exposure to BDNF for indicated times.

Figure 11:
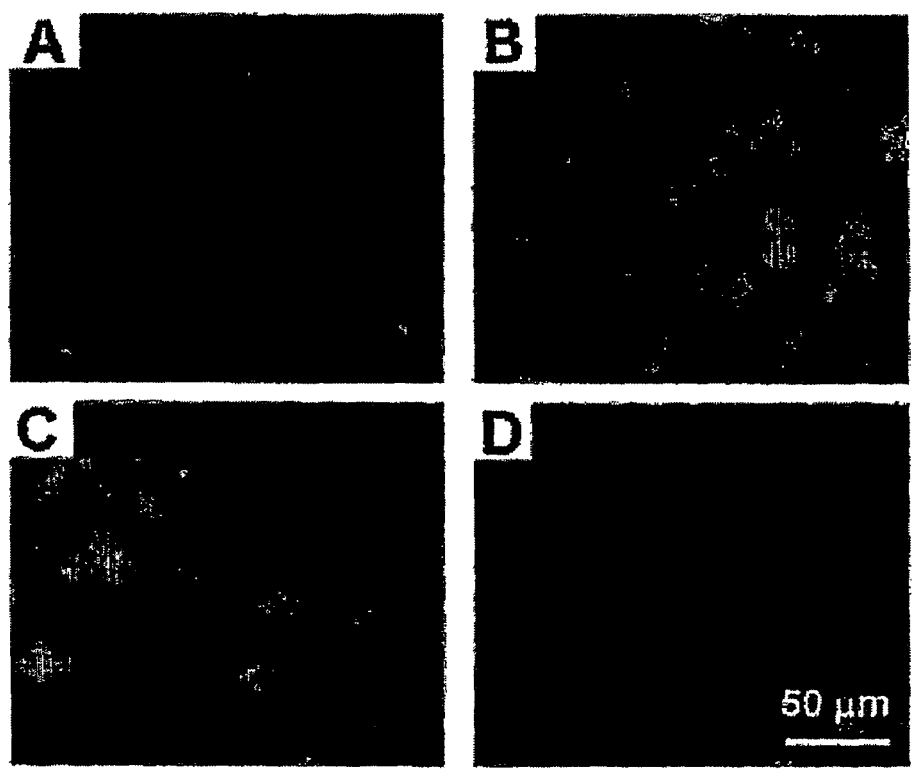
Figure 12:
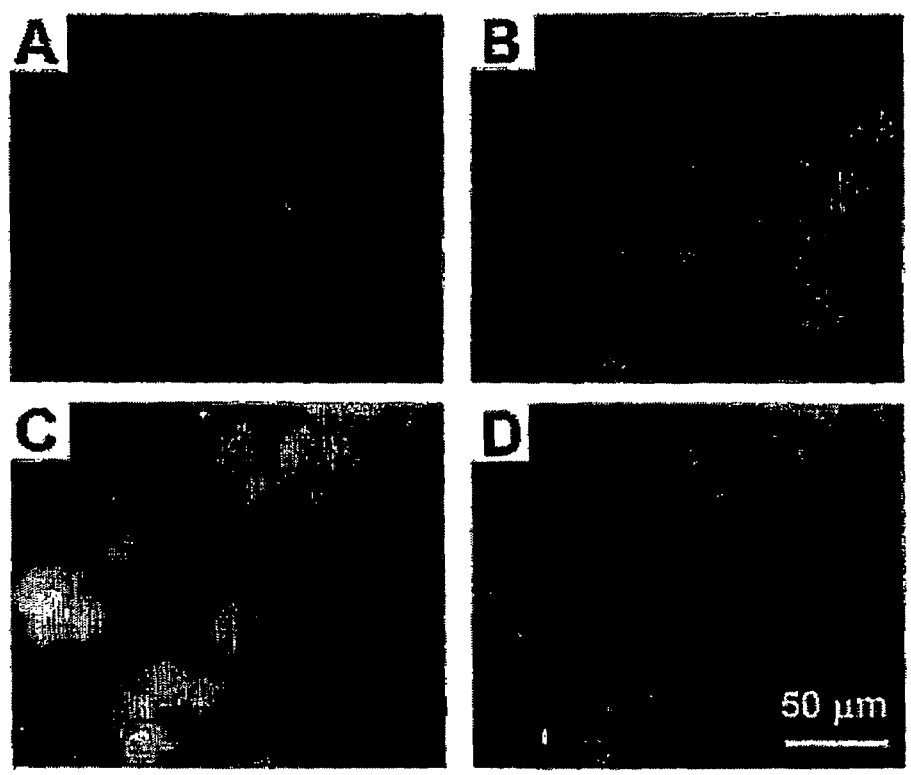
Figure 13:
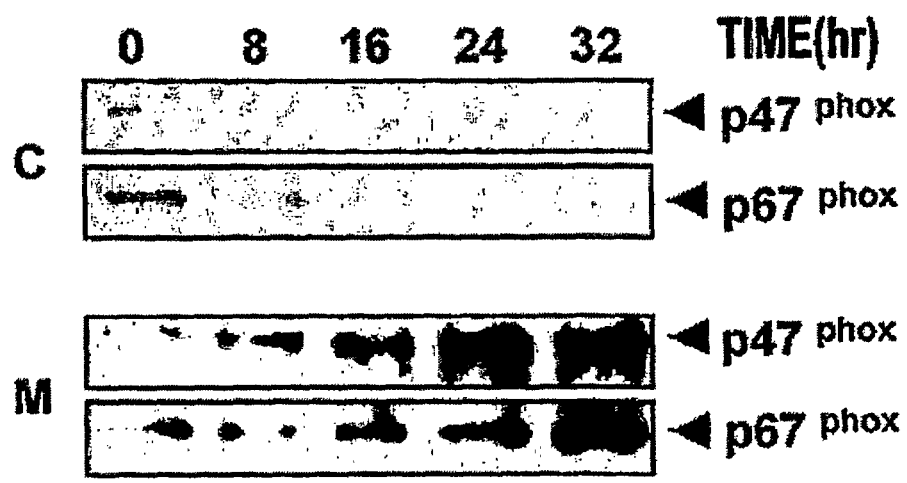

FIG. 11 is a graph showing fluorescence photomicrograph of cortical cell cultures immunolabeled after exposure to a sham wash and BDNF.
A: sham wash, immunolabeling with anti-p47-phox or anti-goat IgG conjugated with FITC
B: sham wash, immunolabeling with NeuN or anti-goat IgG conjugated with Texas red
C: Treatment with BDNF, immunolabeling with anti-p47-phox or anti-goat IgG conjugated with FITC
D: Treatment with BDNF, immunolabeling with NeuN or anti-goat IgG conjugated with Texas red FIG. 12 is a graph showing fluorescence photomicrograph of cortical cell cultures immunolabeled after exposure to a sham wash and BDNF.
A: sham wash, immunolabeling with anti-p67-phox or anti-goat IgG conjugated with FITC
B: sham wash, immunolabeling with NeuN or anti-goat IgG conjugated with Texas red
C: Treatment with BDNF, immunolabeling with anti-p67-phox or anti-goat IgG conjugated with FITC
D: Treatment with BDNF, immunolabeling with NeuN or anti-goat IgG conjugated with Texas red FIG. 13 is a graph showing western blot analysis of the cytosolic fraction (C) and the membrane fraction (M) using anti-p47-phox and anti-p67-phox antibodies that were obtained from cortical cell cultures following exposure to BDNF for indicated times.

Figure 14:
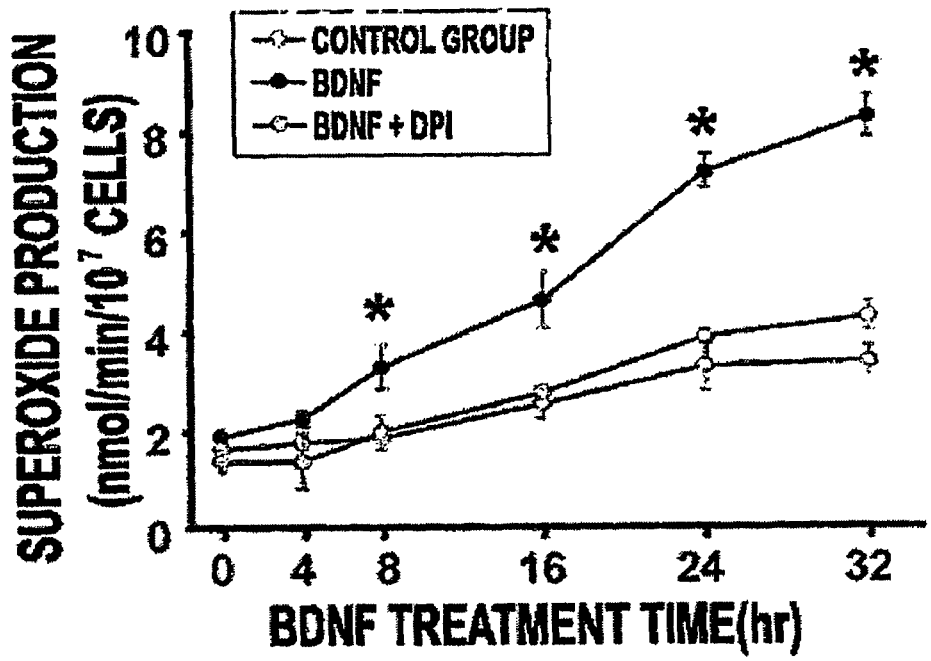

FIG. 14 is a graph showing analysis of superoxide production by measuring reduction of cytochrome c in cortical cultures exposed to a sham wash or BDNF with or without DPI for indicated times.

Figure 15:
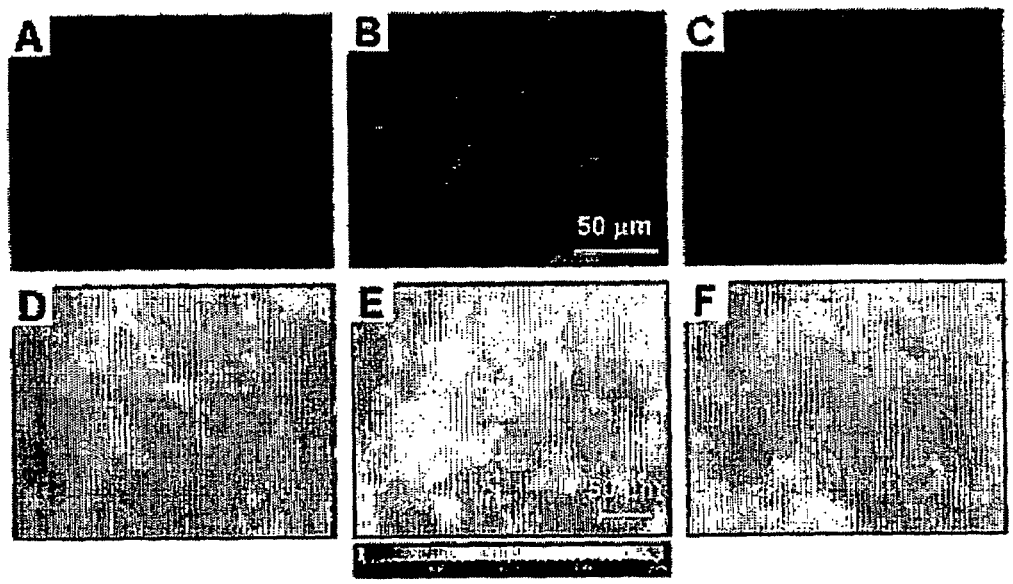
Figure 16:
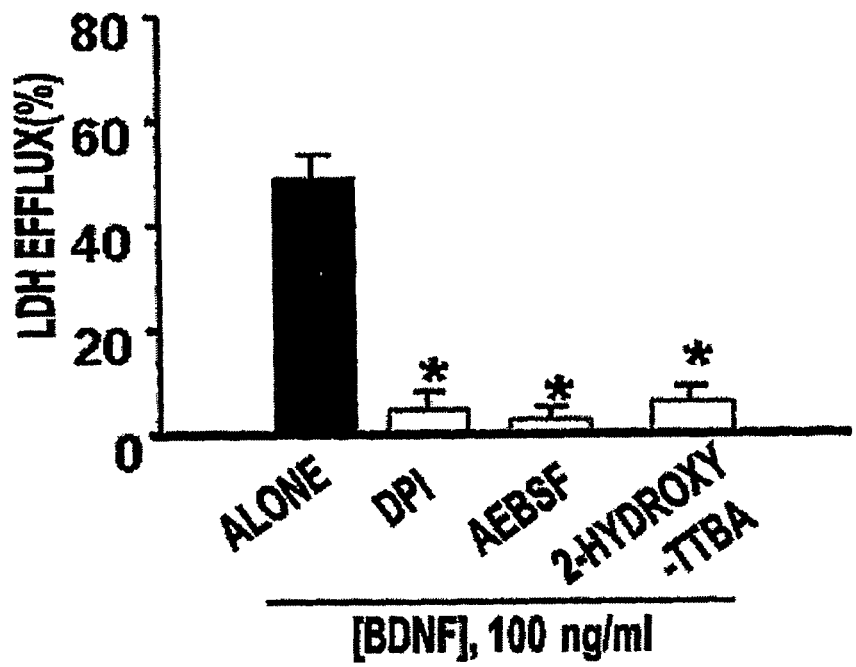

FIG. 15 is a graph showing fluorescence photomicrograph of the oxidized Het and DCF in cortical neurons following exposure to a sham operation, BDNF, or BDNF plus DPI.
A: The oxidized hydroethydine (HEt) in cortical neurons following exposure to a sham operation
B: The oxidized hydroethydine (HEt) in cortical neurons following exposure to BDNF
C: The oxidized hydroethydine (HEt) in cortical neurons following exposure to BDNF plus DPI
D: The oxidized DCF in cortical neurons following exposure to a sham operation
E: The oxidized DCF in cortical neurons following exposure to BDNF
F: The oxidized DCF in cortical neurons following exposure to BDNF plus DPI FIG. 16 is a graph showing analysis of neuronal death by measurement of LDH efflux into the bathing medium in cortical neurons following exposure to BDNF, BDNF+DPI, BDNF+AEBSF or BDNF+2-Hydroxy-TTBA.

Figure 17:
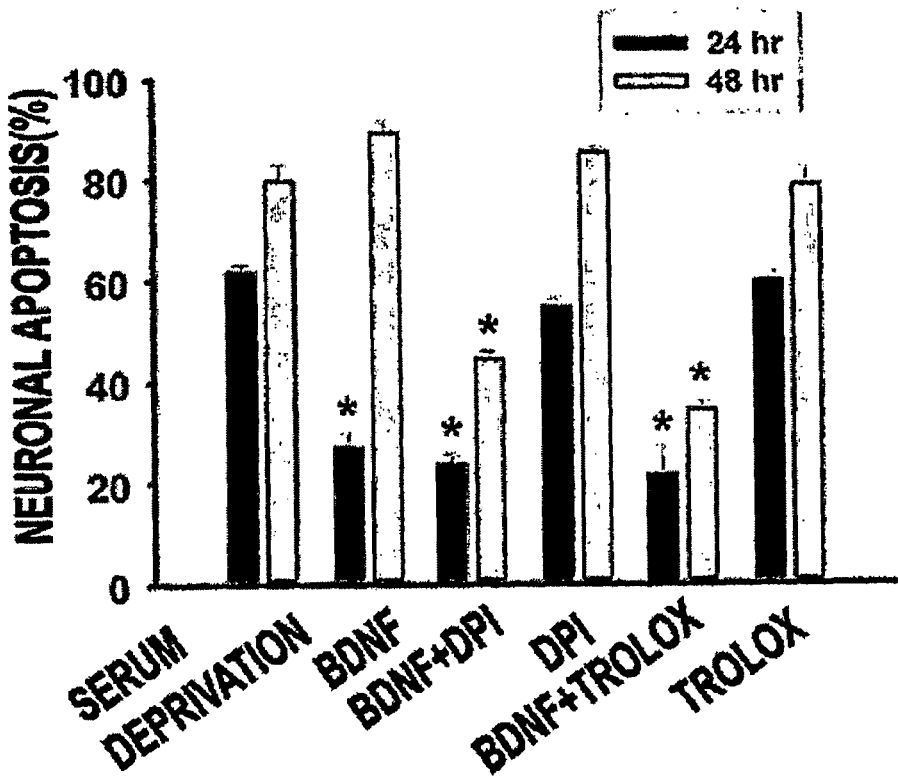

FIG. 17 is a graph showing analysis of neuronal apoptosis in neuron-rich cortical cell cultures following exposure to serum deprivation, alone or in the presence of BDNF, BDNF plus DPI, DPI, BDNF plus trolox, or trolox.

DETAILED DESCRIPTION OF THE INVENTION

The detailed description of the present invention is as follows:

The present invention provides a method for preventing neurotrophin-induced necrosis with administration of drugs that block oxidative stress.

Anti-oxidants in the present invention can be chosen from NADPH oxidase inhibitors, vitamin E, vitamin E analogue or tetrafluorobenzyl derivatives. NADPH oxidase inhibitors can be selected from diphenylene iodonium (DPI) or 4-(2-amonoethyl)-benzensulfonyl fluoride (AEBSF). Vitamin E analogue is trolox, a membrane-permeable form of vitamin E. Tetrafluorobenzyl derivatives can be selected from BAS(5-benzylaminosalicylic acid), TBAS(5-(4-trifluoromethylbenzyl) aminosalicylic acid), NBAS(5-(4nitrobenzyl) aminosalicylic acid), CBAS(5-(4-chlorobenzyl) aminosalicylic acid), MBAS(5-4-methoxybenzyl) aminosalicylic acid), FBAS(5-(4-fluorobenxyl) aminosalicylic acid), and 2-hydroxy-TTBA (2-Hydroxy-5-(2,3,5,6-tetrafluoro-4trifluoromethyl-benzylamino)-benzoic acid.

Neurotrophins in the present invention can be selected from nerve growth factor (NGF), brain-derived neurotrophic factor (BDNF), neurotrophin-3 (NT-3), and NT-4/5, and BNDF is more preferred.

BDNF causes neuronal cell necrosis by inducing expression and activation of NADPH oxidase and subsequent production of reactive oxygen species (ROS).

Administration of DPI or AEBSF prevents BDNF-induced neuronal cell necrosis by inhibiting NADPH oxidase and ROS production. Vitamin E or it analogue trolox prevents BDNF-induced neuronal death by blocking ROS production. Tetrafluorobenzyl derivatives—BAS, TBAS, NBAS, CBAS, MBAS, FBAS, and 2-Hydroxy-TTBA—block free radical neurotoxicity as anti-oxidants (WO 01/79153), which prevents BDNF-induced neuronal death.

Thus, anti-oxidants in the present invention can prevent neurotrophin-induced neuronal cell necrosis.

The present invention provides a method for preventing neuronal apoptosis and necrosis with concurrent administration of neurotrophins and anti-oxidants.

Anti-oxidants in the present invention can be chosen from NADPH oxidase inhibitors, vitamin E, vitamin E analogue or tetrafluorobenzyl derivatives. NADPH oxidase inhibitors can be selected from DPI or AEBSF. Vitamin E analogue is preferably trolox, a membrane-permeable form of vitamin E. Tetrafluorobenzyl derivatives can be selected from BAS, TBAS, NBAS, CBAS, MBAS, FBAS, and 2-Hydroxy-TTBA.

Neurotrophins in the present invention can be selected from brain-derived neurotrophic factor (BDNF), neurotrophin-3 (NT-3), and NT-4/5, and BDNF is more preferred.

While neurotrophins promote neuronal survival by blocking apoptosis but can cause neuronal necrosis through production of ROS. The latter can be blocked by administration of anti-oxidants. Interestingly, concurrent administration of anti-oxidants greatly enhances effects of neurotrophins promoting neuronal survival by blocking the pro-necrotic actions of neurotrophins.

Thus, co-administration of neurotrophins and anti-oxidants can be applied to prevent apoptosis and necrosis in hypoxic-ischemic injury (Holtzman et al., 1996, Ann. Neurol., 39(1), 114-122; Ferrer et al., 2001, Acta neuropathol. (Berl.), 101(3), 229-38), chronic spinal cord injury (Jin et al., 2002, Exp. Neurol., 177(1), 265-75), Alzheimer's disease (Siegel and Chauhan, 2000, Brain Res. Brain Res. Rev., 33, 2-3), Parkinson's disease (Bradford et al., 1999, Adv. Neruol. 80, 19025), ALS (Louvel et al., 1997, Trends. Pharmacol. Sci., 18(6), 196-203), Huntington's disease (Perez-Navarro et al., 2000, J. Neurochem, 75(5),2190-9), glaucoma (Ko et al., 2000, Invest. Ophthalmol. Vis. Sci., 41(10), 2967-71) or retinal detachment (Lewis et al., 1999, Invest. Ophthalmol. Vis. Sci., 40(7), 1530-1544).

The present invention provides an inhibitor for preventing neurotrophin-induced neuronal cell necrosis and thus enhancing survival effects of neurotrophins with administration of tetrafluorobenzyl derivatives.

A drug containing tetrafluorobenzyl derivatives as an effective component can be applied to prevent ROS production and neuronal cell necrosis by neurotrophins. Tetrafluorobenzyl derivatives in the present invention can be selected from BAS, TBAS, NBAS, CBAS, MBAS, FBAS, and 2-Hydroxy-TTBA. Neurotrophins in the present invention can be selected from brain-derived neurotrophic factor (BDNF), neurotrophin-3 (NT-3), and NT-4/5, and BDNF is more preferred.

The composition of the present invention can be treated by oral administration, intravenous injection or non-oral administration, and treated by various forms such as tablet, capsule, powder, grain, sterilized solution, suspension or suppository for rectal administration. Major effective elements of the composition can be made as a solid tablet using pharmaceutical carriers, for example common tablet element such as corn dextrin, lactose, sucrose, sorbitol, talc, stearic acid, magnesium stearate, decalcium phosphate or gums, and additional pharmaceutical diluted solution. Tablets or pillets of the pharmaceutical composition in the present invention can be manufactured for sustained release dosage form as facilitated forms for administration using well-known coating method etc. in the appropriate industry. For example, tablets or pillets can be composed with inner and outer administrative elements. The inner administrative elements of tablets or pillets can be manufactured as wrapped with outer administrative elements. Liquid forms of the composition in the present invention manufactured for oral administration or the injection include solution, appropriately flavored syrup, water-soluble suspension, water-insoluble suspension, emulsion made by edible oil such as cotton oil, sesame oil, coconut oil, or peanut oil, elixir, and similar pharmaceutical carriers. Tragacanth gum, acacia, alginic acid sodium salt, dextran, sodium carboxymethylcellulose, methylcellulose, polyvinylpyrrolidone, or synthesized or natural gums like gelatin etc can be used as appropriated aid to dispersion or suspension in making water-soluble suspension.

Quantity of medication can be determined by several related factors such as diseases, age, sex, weight, and degrees of illness of patients etc. for the treatment of neurodegeneration.

Hereinafter, embodiments of the present invention will be described in detail.

However, the examples described in the schemes are just representative of the present invention, which could include more examples.

EXAMPLE 1

Primary Cortical Cell Cultures

Rat cortical cell cultures were prepared from the 17-day-old fetal brain and the neocortices were mechanically triturated as previously described (Noh and Gwag, 1997). Dissociated cells were plated on 6-well plates and 24-well plates (approximately 3 cortices per plate), or on glass bottom 35 mm dishes for ROS imaging. Plating media consist of Eagle's minimal essential media (MEM, Earle's salts, supplied glutamine-free) supplemented with 5% horse serum, 5% fetal bovine serum, 21 mM glucose, 26.5 mM bicarbonate and 2 mM L-glutamine.

For neuron-glia mixed cultures, 10 μM cytosine arabinoside (Ara C) was included to stop the overgrowth of non-neuronal cells to cultures at DIV 5-7 when glial cells were confluent underneath neurons. After 2 days, cultures were then fed with plating medium lacking fetal serum twice a week. Cultures were maintained at 37° C. in a humidified 5% $CO_2$ incubator. For neuron-rich cultures (>95%), 2.5 μM Ara C was included to cultures at 2-3 days in vitro (DIV 2-3) as previously described (Gwag et al., 1997).

EXAMPLE 2

Induction and Analysis of Cell Death

To examine if neurotrophins would induce neuronal necrosis, BDNF-induced neuronal death was analyzed by measuring the level of lactate dehydrogenase (LDH) released into the bathing medium.

Mixed cortical cell cultures (DIV 12-14) were rinsed in serum free MS (MEM supplemented with 26.5 mM sodium bicarbonate and 21 mM glucose) and then exposed to various concentrations of NGF, BDNF or NT-3 in serum free MS. Neuronal cell death was analyzed by measuring the level of lactate dehydrogenase (LDH) released into the bathing medium. The percent neuronal death was normalized to the mean LDH value released after a sham control (defined as 0%) or continuous exposure to 500 μM NMDA for 24 hr (defined as 100%) The latter produces complete neuronal death within 24 hr. For experiments for serum deprivation, neuron-rich cortical cell cultures (DIV 7) were placed into serum free MS containing 1 μM MK-801 as described (Gwag et al., 1995). Neuronal death was analyzed 24 and 48 hr later by counting viable neurons excluding Trypan Blue satained.

Figure 1:
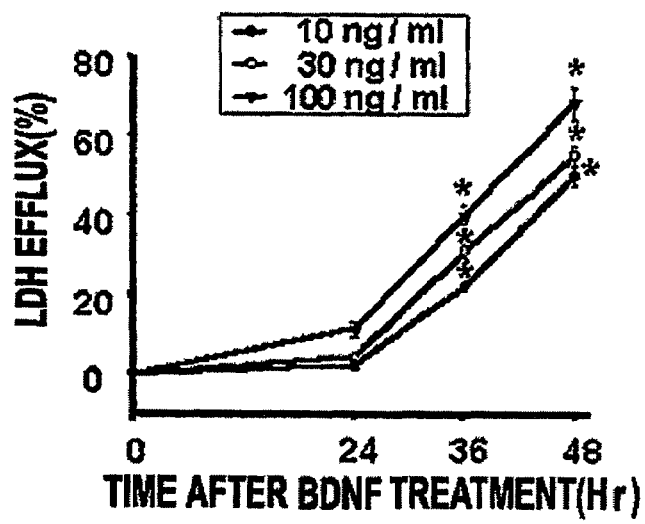
FIG. 1 is a graph showing neurotrophins-induced neuronal necrosis in cortical cell cultures.
Figure 1:
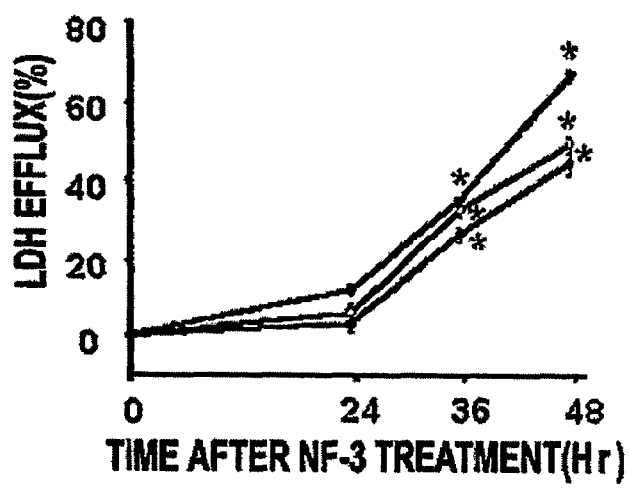
Figure 1:
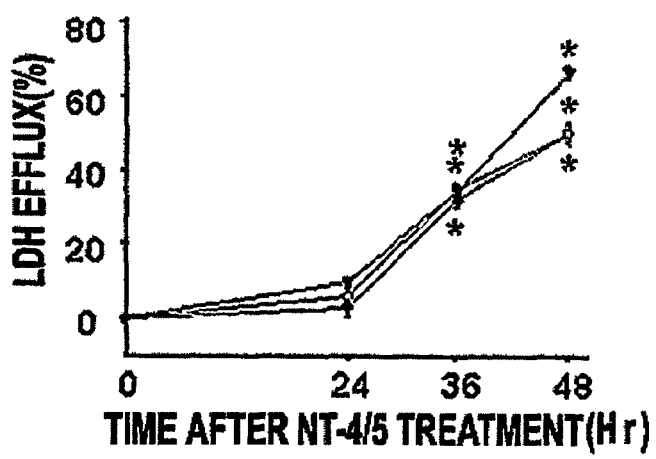

Wide spread neuronal death occurred in cortical cell cultures continuously exposed to various concentrations (10, 30, or 100 ng/ml) of BDNF or NT-3 for 36-48 hr (FIG. 1A). Near complete neuronal death was observed within 48 hr after exposure to BDNF or NT-3 (FIG. 1). Neuronal cell death was assessed by measurement of LDH efflux to the bathing medium, mean±SEM (n=16 culture wells per condition). *, Significant difference from the relevant control (sham washed control), at $P<0.05$ using analysis of variance and Student-Newman-Keuls test.

Thus, it is found that neurotrophin such as BDNF, NT-3 and NT-4/5 derives cell necrosis.

EXAMPLE 3

Intrastriatal Injection of BDNF in Rat Brain

To confirm BDNF-induced neuronal necrosis, adult male Sprague-Dawley rats weighing 250-300 g were anesthetized intraperitoneally with chloral hydrate (400 mg/ml). Animals were placed in a Kopf stereotaxic apparatus and injected with 1 g/l of BDNF (dissolved in 0.9% NaCl (saline)), or saline alone in the striatum at the following coordinates: 1.0 mm rostral to bregma, 3.0 mm lateral to the midline, and 5.0 mm ventral from the dural surface. For each injection, a volume of 5 µl was delivered for 10 min via 10 µl Hamilton syringe. Three minutes were allowed prior to syringe withdrawal and wound closure. These rats were euthanized 2 d later. Animals were anaesthetized, and then perfused transcardially with phosphate-buffered saline (PBS) followed by 3% paraformaldehyde. The brains were immediately removed, post-fixed, and then sectioned (8 µm) on a microtome (TPI, Inc., MO). Sections including the injection site were collected and stained with Hematoxylin and Eosin (H&E). The lesion area was analyzed as previously described (Won et al., 2000). Six serial sections including the needle track and the largest injury area evident by decrease in staining intensity were included for analysis of injury per each animal.

The striatal section stained with H&E was scanned analyzed using a computer-assisted image analysis system (SigmaScan, Calif./TINA 2.0, KAIST, Daejeon, Korea). The neurotoxic effects of NTs were observed in striatal areas 2d after the intrastriatal injections of BDNF in adult rat brain (FIG. 2).

EXAMPLE 4

Transmission Electron Microscopic Observation

To examine the patterns of BDNF-induced neuronal death, we observed neurons from 32 hrs after a sham wash or continuous exposure to 100 ng/ml BDNF under phase contrast or transmission electron microscope.

Cultures were fixed in Karnovskys fixative solution (1% paraformaldehyde, 2% glutaraldehyde, 2 mM calcium cholride, 100 mM cacodylate buffer, pH 7.4) for 2 hr, washed with cacodylate buffer, and post-fixed in 1% osmium tetroxide and 1.5% potassium ferrocyanide for 1 hr. Cells were then stained en bloc in 0.5% uranyl acetate, dehydrated through graded ethanol series, and embedded in Poly/Bed 812 resin (Pelco, Calif.). Cells were sectioned using Reichert Jung Ultracut S (Leica, Cambridge, UK). After staining cells with uranyl acetate and lead citrate, cells were observed and photographed under Zeiss EM 902A.

The ultrastructural analysis of degenerating neurons in BDNF-treated cortical cultures reveals swelling of cytoplasmic organelles, earlier collapse of plasma membrane than nuclear membrane, and scattering condensation of nuclear chromatin (FIGS. 3 and 4). Neurons from control and BDNF-treated cultures were selected and observed under transmission electron microscope and degenerating neurons were defined as normal, necrosis, or apoptosis (shinkage of cytoplasm and nuclear membrane rupture with intact plasma membrane), suggesting that BDNF induced neuronal necrosis.

EXAMPLE 5

BDNF Produces ROS in Cortical Neurons

Many studies imply that increased reactive oxygen species (ROS) induced neuronal necrosis, we examined if BDNF-induced neuronal necrosis would produce ROS.

Cortical cell cultures (DIV 12-15) grown on glass bottom dishes were loaded with 10 µM dichlorodihydro fluorescein diacetate (DCDHF-DA) or 5 µM hydroethidium (Molecular Probes, Eugene, Oreg.) plus 2% Pluronic F-127 in HEPES-buffered control salt solution (HCSS) buffer containing (in mM): 120 NaCl, 5 KCl, 1.6 $MgCl_2$, 2.3 $CaCl_2$, 15 glucose, 20 HEPES, and 10 NaOH. Cultures were incubated for 20 min at 37° C., and washed three times with HCSS buffer. The fluorescence signal of oxidized DCDHF was observed at room temperature on the stage of a Nikon Diaphot inverted microscope equipped with a 100 W xenon lamp and filter (for oxidized DCDHF, excitation=488 nm and emission=510 nm; for hydroethidine, excitation=546 nm and emission=590 mm). The fluorescence images were analyzed using a QuantiCell 700 system (Applied imaging, UK).

The fluorescent intensity of DCF was increased in cortical neurons exposed to BDNF for 16 hr (FIG. 6). The intraneuronal levels of ROS ($[ROS]i$) were further increased over 24-32 hr. The BDNF-induced production of $[ROS]_i$ was prevented by concurrent addition of cycloheximide as well as trolox (FIG. 7).

Thus, BDNF likely produces ROS presumably through synthesis of pro-oxidant proteins.

EXAMPLE 6

BDNF-induced Neuronal Necrotic Mechanism

To examine BDNF-induced neuronal necrotic mechanism, cortical cell cultures (DIV 12-15) were continuously exposed to 100 ng/ml BDNF, alone or with 100 µg/ml anti-BDNF blocking antibody, 100 µM trolox, or 1 µg/ml cycloheximide (CHX, and neuronal death was analyzed 36 hr later by measurement of LDH efflux into the bathing medium. Concurrent administration of anti-BDNF blocking antibody completely blocked BDNF neurotoxicity.

Interestingly, BDNF-induced neuronal cell necrosis was also blocked by addition of cycloheximide, a protein synthesis inhibitor and trolox, a lipophilic analogue of vitamin E (FIG. 5). {mean±SEM (n=16 culture wells per condition). *, Significant difference from the relevant control (BDNF alone), at P<0.05 using analysis of variance and Student-Newman-Keuls test.}

Thus, neuroprotective effect against BDNF-induced neuronal necrosis was accompanied by blockade of reactive oxygen species (ROS) production.

EXAMPLE 7

Genes Expressed in Rat Cortical Cell Cultures Treated with BDNF (7-1) cDNA Microarray Analysis We used cDNA microarray assay to screen target genes for the pro-oxidant action of BDNF in cortical cell cultures.

Total RNA was isolated from cortical cell cultures (DIV 12) by using RNA zol B (Tel-Test INC., Friendswood, Tex.). Approximately 1 µg of total RNA was used to synthesize cDNA labeled with [$\alpha$-$^{33}$p] dATP that was hybridized to rat gene filter membranes (Research Genetics, Huntsville, Ala.) at 42° C. for 12-18 hr. The membranes were washed in 2× saline sodium citrate (SSC) buffer and 1% sodium dodecyl sulfate (SDS) at 50° C. for 20 min, 0.5×SSC and 1% SDS at room temperature for 15 min, and then wrapped up in plastic wrap and apposed to a phosphorimager cassette. After exposure of gene filters, the hybridization pattern was analyzed using Pathways™ 4-universal microarray analysis software Invitrogen, Netherlands).

The microarray analysis revealed that various genes were regulated in cortical cell cultures exposed to BDNF for 8 hr (Table 1). The target genes of BDNF mostly play a role in differentiation, endocytosis, metabolism, and signal transduction that likely reflect neurotrophic actions of neurotrophins. Among the BDNF-sensitive genes, cytochrome $b_{558}$ was chosen as a candidate gene for the neurotoxic actions of the NTs, since it constitutes p22-phox and gp91-phox subunits of NADPH oxidase, a pro-oxidant enzyme generating superoxide from oxygen.

(7-2) Reverse Transcription—Polymerase Chain Reaction (RT-PCR)

RT-PCR experiments were performed to confirm the BDNF-sensitive genes derived from cDNA expression microarray, cytochrome $b_{558}$ as it constitutes p22-phox and gp91-phox subunits of NADPH oxidase, a pro-oxidant enzyme generating superoxide from oxygen.

Total RNA (1 μg each) was incubated in a reaction mixture containing dNTP (2.5 mM each), RNasin (0.5 Unit), oligo dT primer (100 ng), and MMLV reverse transcriptase (200 Unit) at 37° C. for 1 hr. The samples were incubated at 92° C. for 10 min and transferred to 4° C. The reverse transcribed cDNA was subjected to PCR amplification. PCR was performed according to manufacturer's procedure (Takara Shuzo Co., Japan) sequentially (denaturation-annealing-extension) at following conditions: for p47-phox, 94° C. for 30 S, 55° C. for 30 S, and 72° C. for 60 S (28 cycles); for p22-phox (homologous to cytochrome $b_{558}$ in microarray) and gp91-phox, 94° C. for 45 S, 60° C. for 60 S, and 72° C. for 120 S (33 cycles); for GAPDH, 94° C. for 35 S, 55° C. for 45 S, and 72° C. for 90 S (25 cycles). Primer sequences used were as follows (5'-3'): for p22-phox, GAATTCCGATGGGGCAGATC-GAGTGGGCCA (forward) and GGATCCCGT CACAC-GACCTCATCTGTCACT (reverse); for p47-phox, CAGCCA GCACTATGTGTACA (forward) and GAACTCGTAGATCTCGGTGAA (reverse); for gp91-phox, GAATTCCGATGGGGAACTGGGCTGTGAA TG (forward) and GGATCCCGTTAGAAGTTTTCCTTGT-TGAAA (reverse); for GAPDH, TCCATGACAACTTTG-GCATCGTGG (forward) and GTTGCTGTTGAAGTCA-CAGGAGAC (reverse). PCR products were run on a 1.2% agarose gel and visualized with ethidium bromide. The relative amount of mRNA was measured using LAS-1000 systems (Fuji Photofilm Co., Japan), normalized to levels of GAPDH mRNA. DNA sequencing was performed with Big Dye Terminator Chemistry from Perkin-Elmer Applied Biosystems on ABI PRISM™ 377 DNA sequencer (Foster City, Calif.)

Reverse transcription-polymerase chain reaction (RT-PCR) analysis showed increase in mRNA levels of p22-phox and gp91-phox within 2 hr after treatment with BDNF. Levels of both mRNAs were maximally increased 4 hr later, which lasted over the next 12 hr. The mRNA levels of p47-phox subunit were also increased gradually from 30 min following administration of BDNF (FIGS. 8 and 9).

Thus, BDNF appears to increase expression of NADPH oxidase.

(7-3) Western Blot Analysis

Western blot experiments were performed to analyze protein levels of NADPH oxidase subunits using available antibodies for gp91-phox, p47-phox, and p67-phox.

Cortical cell cultures were lysed in a lysis buffer containing 50 mM Tris-HCl (pH 7.5), 1% Nonidet P-40, 150 mM NaCl, 0.5% deoxycholic acid, 0.1% sodium dodecyl sulfate (SDS), 1 mM PMSF (phenylmethylsulfonyl fluoride), 10 μg/ml pepstain A, and 100 μg/ml leupeptin. Cell lysates were centrifuged at 12,000 g for 10 min. approximately 25 μg of protein was subjected to electrophoresis on 12% SDS-polyacrylamide gel and transferred to a nitrocellulose membrane. The blot was incubated in 2.5% bovine serum albumin for 1 hr, incubated with goat polyclonal primary antibodies, anti-gp91-phox, anti-p67-phox, or anti-p47-phox antibodies (1:1000, Santa Cruz, Santa Cruz, Calif.), and then reacted with a biotinylated anti-goat secondary antibody. Immunoreactivity was detected with Vectastain ABC kit (Vector Laboratory, Burlingame, Calif., USA) and luminol for enhanced chemiluminescence Intron, Korea). The signal was analyzed by quantitative densitometry using LAS-1000 systems (Fuji Photofilm Co., Japan).

Protein levels of NADPH oxidase subunits, gp91-phox, p47-phox, and p67-phox, was increased over 16-32 hr in cortical cell cultures exposed to BDNF (FIG. 10).

Thus, BDNF appears to express protein levels of NADPH oxidase.

(7-4) Immunocytochemistry

Immunocytochemistry was performed to identify which types of cells express NADPH oxidase in cortical cell cultures containing neurons and glia.

Cortical cell cultures (DIV 12-14) grown on glass bottom dishes were fixed in 4% paraformaldehyde for 30 min, incubated in 10% horse serum for 1 hr, and double-immunolabeled with a mouse monoclonal antibody against NeuN (1:400 dilution, Chemicon, Temecula, Calif.) and a goat polyclonal antibody against p47-phox or p67-phox (1:200 dilution, Santa Cruz, Santa Cruz, Calif.) for 2-4 hr. Cultures were then reacted with fluorescein isothiocyanate-conjugated anti-goat IgG (1:200 dilution, Organon Teknika Corp., NC) and Texas red-conjugated anti-mouse IgG (1:200, Vector Laboratory, Burlingame, Calif.) for 1-2 hr. The fluorescence images were collected and analyzed with a fluorescence microscopy (Zeiss, Germany) equipped with the Real-14™ precision digital camera (Apogee Instrument, Tucson, Ariz.) and ImagePro Plus Plug-in (Silver Spring, Md.).

Immunoreactivity to p47-phox or p67-phox antibody was slightly observed in cortical neurons but not in astrocytes following a sham operation. Signals of p47-phox and p67-phox were increased exclusively in neurons 32 hr following exposure of cortical cell cultures to BDNF (FIGS. 11 and 12).

(7-5) Subcellular Fractionation

Activation of NADPH oxidase involves translocation of the cytosolic p47-phox and p67-phox subunits into the plasma membrane (Clark et al., 1989, *Trans. Assoc. Am. Physicians.*, 102, 224-230). We examined if treatment with BDNF would activate NADPH oxidase through isolating the cytosol and membrane fraction.

Cortical cell cultures were washed with ice-cold PBS and resuspended in an isotonic buffer containing 10 mM HEPES, pH 8.0, 250 mM sucrose, 1 mM EDTA, 1 mM EGTA, 1 mM dithiothreitol (DTT), 2 mM PMSF, 100 μg/ml leupeptin, and 10 μg/ml pepstatin A. For isolating the cytosol and membrane fraction, the lysate was homogenized with a homogenizer (KONTE, Vieland, N.J.), centrifuged at 9,000 g for 10 min, and the supernatant was then centrifuged at 100,000 g for 1 hr.

The membrane fraction was obtained by resuspending the pellet with 50 μl lysis buffer and the cytosolic fraction was obtained from the supernatant. As shown in <EXAMPLE 7-4>, western blot experiments were performed to analyze protein levels of NADPH oxidase subunits using available antibodies for gp91-phox, p47-phox, and p67-phox.

The levels of p47-phox and p67-phox were reduced in the cytosolic fraction and increased in the membrane fraction from cortical cell cultures exposed to BDNF for 16-32 hr (FIG. 13), suggesting that treatment with BDNF-induced activation of NADPH oxidase was increased in the membrane fraction, and induced oxidative stress in cortical neurons through production of ROS.

EXAMPLE 8

Measurement of NADPH Oxidase Activity in BDNF-treated Corical Cell Cultures

We examined if activation of NADPH oxidase would contribute to BDNF-induced neuronal death.

Superoxide production was measured in a quantitative kinetic assay based on the reduction of cytochrome c (Mayo and Curnutte, 1990). Cortical cell cultures were suspended in PBS and incubated in a reaction mixture containing 0.9 mM $CaCl_2$, 0.5. mM $MgCl_2$, and 7.5 mM glucose, 75 μM cytochrome c (Sigma, St. Louis, Mo.), and 60 μg/ml super oxide dismutase (Sigma, St. Louis, Mo.) for 3 min at 37° C. The superoxide production was determined by measuring the absorbance of cytochrome c at 550 nm using a Thermomax microplate reader and associated SOFTMAX Version 2.02 software (Molecular Devices Corp., Menlo Park, Calif.).

Co-administration of NADPH oxidase inhibitors, 3-10 nM DPI or 10-30 μM 4-(2-amonoethyl)-benzensulfonyl fluoride (AEBSF), significantly reduced swelling of neuronal cell body and neuronal death 36 hr after exposure of cortical cell cultures to BDNF (FIG. 14).

Thus, the NADPH oxidase-mediated production of superoxide was reduced in the presence of the selective inhibitors of NADPH oxidase.

EXAMPLE 9

BDNF Produces ROS Through Activation of NADPH Oxidase

NADPH oxidase was first discovered in phagocytes as a superoxide-producing enzyme via one-electron reduction of oxygen. We performed to examine whether BDNF would produce ROS through activation of NADPH oxidase.

Superoxide production through activation of NADPH oxidase was analyzed by measuring the oxidation of HEt and DCDHF to ethidium and DCF, respectively, in cortical neurons after exposure to a sham operation, 100 ng/ml BDNF, or 100 ng/ml BDNF plus 3 nM DPI for 32 hr (FIG. 15). Treatment with BDNF resulted in the increased oxidation of Het and DCDHF, DPI completely blocked BDNF-induced superoxide production (FIG. 15).

Thus, BDNF produces oxidative stress in cortical neurons through NADPH oxidase-mediated production of superoxide.

EXAMPLE 10

Activation of NADPH Oxidase Mediates BDNF Neurotoxicity

We examined if activation of NADPH oxidase would contribute to BDNF-induced neuronal death.

Cortical cell cultures (DIV 12-15) were exposed to 100 ng/ml BDNF, alone or in the presence NADPH oxidase inhibitors, 3-10 nM DPI, 10-30 μM 4-(2-amonoethyl)-benzensulfonyl fluoride (AEBSF), or 1 μM 2-Hydroxy-TTBA ((2-Hydroxy-5-(2,3,5,6-tetrafluoro-4-trifluoromethyl-benzylamino)-benzoic acid). Neuronal death was analyzed 36 hr later by measurement of LDH efflux into the bathing medium.

Co-administration of 3 nM DPI, 10 μM AEBSF, or 1 μM 2-Hydroxy-TTBA significantly reduced neuronal necrosis 36 hr after exposure of cortical cell cultures to BDNF (FIG. 16). Mean±SEM (n=16 culture wells per condition). *, Significant difference from the relevant control (BDNF alone), at $P<0.05$ by Student-Newman-Keuls test.

Thus, the neurotrophic effect of BDNF is enhanced with blockade of oxidative stress by NADPH inhibitors or antioxidants.

EXAMPLE 11

Antiapoptotic Action of NTs

It has been reported that BDNF prevent neuronal apoptosis. As previously reported, we examined if blocking action of BDNF, such as inhibitor of NADPH oxidase or antioxidant, would affect BDNF-induced neuronal necrosis.

Neuron-rich cortical cell cultures (DIV 7) were deprived of serum, alone (serum deprivation) or in the presence of 100 ng/ml BDNF, 100 ng/ml BDNF plus 3 nM DPI, 3 nM DPI, 100 ng/ml BDNF plus 100 μM trolox, or 100 μM trolox. Neuronal death was assessed 24 hr and 48 hr later by counting viable neurons.

Neither DPI nor trolox alone reduced serum deprivation-induced neuronal apoptosis. The anti-apoptotic action of BDNF was insensitive to inclusion of DPI or trolox. Interestingly, the protective effects of BDNF disappeared within 48 hrs following serum deprivation. The delayed neuronal death evolving in the presence of BDNF attenuated by concurrent addition of DPI or trolox (FIG. 17). Mean±SEM (n=16 fields randomly chosen from four culture wells per condition). *, Significant difference from the relevant control (serum deprivation alone), at $P<0.05$ using analysis of variance and Student-Neuman-Keuls test.

Administration of BDNF prevented neuronal apoptosis, but prolonged exposure to BDNF produces neuronal cell necrosis without blocking anti-apoptosis action of BDNF.

Above results show that BDNF-induced expression and activation of NADPH oxidase cause oxidative neuronal necrosis and that the neurotrophic effects of NTs can be maximized under blockade of the pronecrotic action. The concrete diseases applicable with antioxidants or its neurotrophins are described as follows.

Application examples described below are part of examples of this invention. This invention is not limited to application examples.

APPLICATION EXAMPLE 1

Alzheimer's Disease (AD)

The degeneration of glutamatergic neurons in the cerebral cortex and hippocampal formation and of cholinergic neurons in the basal forebrain, extracellular deposit of amyloid plaque, and intracellular neurofibrillary tangles are pathological features of AD. The ability of neurotrophins (e.g., nerve growth factor [NGF]) to promote the survival and phenotype of subsets of central nervous system (CNS) neurons vulnerable in AD, such as basal forebrain cholinergic neurons suggests the use of these molecules to treat neurodegeneration associated with human diseases (Hefti, 1994, *J Neurobiol.*, 25, 1418-1435). In AD, the production of lipid peroxidation, 8-hydroxy deoxyguanosine, protein-carbonyls, nitration, or oxidative crosslinking of proteins by excess generation of free radicals has been reported, suggesting that oxidative stress plays a causative role in neuronal death in AD [Vitek et al., *Proc. Natl. Acad Sci. U.S.A.*, 91:4766-4770 (1994); Smith et al., *Trends. Neurosci.*, 18:172-176 (1995); *Mol. Chem. Neuropathol.*, 28:4148 (1996), *Proc. Natl. Acad Sci. U.S.A.*, 94:9866-9868 (1997); Montine et al., *J. Neuropathol. Exp. Neurol.*, 55:202-210 (1996)]. As a matter of fact, the therapeutic effects of anti-oxidants have been extensively investigated in AD patients. $Zn^{2+}$ is accumulated in the brain (amygdala, hippocampus, inferior parietal lobule, superior and middle temporal gyri) of AD patients, mainly in the center and surround of amyloid plaque and induces aggregation of beta amyloid [Lovell et al., *J. Neurol. Sci.*, 158:47-52 (1998)]. Therefore, the compounds in the present invention showing protective effect against oxidative stress and $Zn^{2+}$ toxicity can be used as therapeutic drugs for AD.

APPLICATION EXAMPLE 2

Parkinson's Disease (PD)

PD is a neurodegenerative disease showing the disorder of motor function by a selective death of dopaminergic neurons in the substantia nigra. In PD patients, oxidative stress has been proved as a main mechanism of neuronal cell death, and the production of lipid peroxidation, 8-hydroxy deoxyguanosine, protein carbonyls or nitration has been reported, suggesting that oxidative stress plays a causative role in neuronal death in PD (Tatton and Kish, 1997, *Neuroscience*, 77, 1037-1048; He et al., 2000, *Brain Research*, 858, 163-166; Turmel et al., 2001, *Mov. Disord.*, 16, 185-189). Many in vivo studies have shown that there is some evidence for the occurrence of apoptosis in the parkinsonian substantia and neurotrophins such as BDNF or GDNF (Glial cell-derived neurotrophic factor) also prevents the death of dopaminergic neurons in vivo (Bradford et al., 1999, *Adv. Nerurol.*, 80, 19-25; Levivier et al., 1995, *J. Neurosci.*, 15, 7810-7820; Olson, 1996, *Nat. Med*, 2, 400-401; Gash et al., 1996, *Nature*, 380, 252-255).

Therefore, the compounds in the present invention showing neurotrophic effects of NTs and antioxidant effects can be used as therapeutic drug for PD.

APPLICATION EXAMPLE 3

Amyotrophic Lateral Sclerosis

Amyotrophic lateral sclerosis (ALS) is an adult-onset neurological disorder that is characterized by the selective degeneration of lower and/or upper motor neurons leading to progressive weakness, atrophy of skeletal muscles and eventual paralysis and death within 2-5 years of clinical onset. Autosomal-dominant familial ALS (FALS) have point mutations in the gene that encodes Cu/Zn superoxide dismutase (SOD1), and protein carbonyl content, a marker of oxidative damage, was elevated in the SALS patients relative to the control patients (Bowling et al., 1993, *J. Neurochem.*, 61, 2322-2325). Recently, clinical trial of BDNF has failed to show beneficial effects in amyotrophic lateral sclerosis (Apfel et al., 2001, *Clin. Chem. Lab. Med*, 39(4), 351-61). This unfavorable effects may be attributable to oxidative neuronal death by the neurotrophin. Thus, the concurrent administration of neurotrophins and anti-oxidants can be applied to effectively treat ALS.

APPLICATION EXAMPLE 4

Hypoxic-ischemic Injury

Stroke occurs when local thrombosis, embolic particles, or the rupture of blood vessels interrupts the blood flow to the brain. During hypoxic-ischemia, membrane depolarization triggers excess $Ca^{2+}$ influx in neurons and glia, reflecting subsequent accumulation of $Ca^{2+}$ in mitochondria ($[Ca^{2+}]m$). Excess $Ca^{2+}$ in the mitochondria results in the production of flee radicals. Accumulated ROS in cells are expected to randomly attack DNA, lipid, and protein; therefore, they contribute to hypoxic-ischemic neuronal necrosis. The pharmacological or genetic intervention of ROS and RNS has been neuroprotective against hypoxic-ischemic neuronal necrosis. (Holtzman et al., 1996, *Ann. Neurol.*, 39(1), 114-122; Ferrer et al., 2001, *Acta neuropathol.(Berl.)*, 101(3), 229-38; Hall et al., 1990, *Stroke*, 21, 11183-11187). As DNA ladders, TUNEL-positive neurons and chromatin condensation were observed in the process of neuronal death in the hypoxic-ischemic brain areas; apoptosis, as well as necrosis, have been considered as additional types of hypoxic-ischemic neuronal death. Thus, the concurrent administration of neurotrophins and anti-oxidants can be applied to effectively treat hypoxic-ischemic injury.

APPLICATION EXAMPLE 5

Chronic Spinal Cord Injury

Traumatic injuries to spinal cord cause tissue damage, in part by initiating reative biochemical changes. Numerous studies have provided considerable support for lipid peroxidation reactions, Ca2+ influx, and disruption of membrane in the spinal cord injury (Brown and Hall, 1992, *J. Am. Vet. Med. Assoc.*, 200, 1849-1859; Springer et al., 1997, *J. Neurochem.*, 68, 2469-2476; Juurlink and Paterson, 1998, *J. Spinal cord Med.*, 21, 309-334), recent evidences provide that neuronal necrosis such as, glutamate excitotoxicity, Ca2+ overload, and oxidative stress, also causes secondary damage, and that special Caspase 3 enzyme inhibitor can apparently decrease the neuronal apoptosis in brain trauma model (Zhang et al., 1990, *J. Neurochem.*, 59, 733-739). Thus, the concurrent administration of neurotrophins and anti-oxidants can be applied to effectively treat chronic spinal cord injury.

APPLICATION EXAMPLE 6

Huntington's Disease (HD)

Striatal projection neurons are highly vulnerable to apoptosis in HD, and oxidative stress contributes to apoptosis of striatal projection, neurotrophic fators are protein that support the survival of neurons, maintain their functions and protect them from different types of insults. Recent reports have shown that grafting of the neurotrophins such as GDNF or BDNF-secreting cell line, protects striatal projection neurons in a rat model of Huntington's disease (Perez-Navarro et al., 2000, *J. Neurochem.*, 75(5), 2190-9). Therefore, the compounds in the present invention showing neuroprotective effects of coadministration with neurotrophins and antioxidants can be used as therapeutic drugs for HD.

APPLICATION EXAMPLE 7

Glaucoma and Retinal Detachment

Glaucoma is a chronic, progressive optic neuropathy often leading to blindness. Elevated intraocular pressure (IOP) is the most important risk factor for progression of glaucomatous damage. Death of retinal ganglion cells (RGCs) in glaucomatous eyes occurs by apoptosis as demonstrated in different species. Reduction of IOP remains the most common treatment for glaucoma. Recent studies provide that free radical scavengers and neurotrophins and other growth factors promote RGC survival and control damage induced by elevated IOP in animal models (Ko et al., 2000, *Invest. Ophthalmol. Vis. Sci.*, 41(10), 2967-71). Recent evidences provide that BDNF may aid in the recovery of the retina after reattachment by maintaining the surviving photoreceptor cells, by reducing the gliotic effects in Muller cells, and perhaps by promoting outer segment regeneration (Lewis et al., 1999, *Invest. Ophthalmol. Vis. Sci.*, 40(7), 1530-1544). Thus, the concurrent administration of neurotrophins and anti-oxidants can be applied to effectively treat glaucoma and retinal detachment.

INDUSTRIAL APPLICABILITY

As anti-oxidants used in the present invention block neurotrophin-induced neuronal necrosis without influencing anti-apoptosis actions of neurotrophins, concurrent administration of anti-oxidants and neurotrophins can be applied to prevent neuronal injury and to promote regeneration in acute brain diseases such as stroke and trauma as well as neurodegenerative diseases such as Alzheimer's disease and Parkinson's disease.

What is claimed is:

1. A composition for enhanced promotion of neuronal survival wherein the composition comprises brain-derived neurotrophic factor (BDNF) and 2-hydroxy-5-(2,3,5,6-tetrafluoro-4-trifluoromethyl-benzylamino)-benzoic acid.

2. The composition according to claim 1, further including a pharmaceutical carrier.

* * * * *

SEQUENCE LISTING

<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: p22-Phox forward primer

<400> SEQUENCE: 1
gaattccgat ggggcagatc gagtgggcca                    30

<210> SEQ ID NO 2
<211> LENGTH: 30
<212> TYPE: DNA
<213> ORGANISM: Artificial Sequence
<220> FEATURE:
<223> OTHER INFORMATION: p22-phox reverse primer

<400> SEQUENCE: 2
ggatcccgtc acacgacctc atctgtcact                    30

<210> SEQ ID NO 3
<211> LENGTH: 20
<212> TYPE: DNA
<213> ORGANISM: Artificial Sequence
<220> FEATURE:
<223> OTHER INFORMATION: p47-phox forward primer

<400> SEQUENCE: 3
cagccagcac tatgtgtaca                               20

<210> SEQ ID NO 4
<211> LENGTH: 21
<212> TYPE: DNA
<213> ORGANISM: Artificial Sequence
<220> FEATURE:
<223> OTHER INFORMATION: p47-phox reverse primer

<400> SEQUENCE: 4
gaactcgtag atctcggtga a                             21

<210> SEQ ID NO 5

```
<211> LENGTH: 30
<212> TYPE: DNA
<213> ORGANISM: Artificial Sequence
<220> FEATURE:
<223> OTHER INFORMATION: gp91-phox forward primer

<400> SEQUENCE: 5
gaattccgat ggggaactgg gctgtgaatg                                    30

<210> SEQ ID NO 6
<211> LENGTH: 30
<212> TYPE: DNA
<213> ORGANISM: Artificial Sequence
<220> FEATURE:
<223> OTHER INFORMATION: gp91-phox reverse primer

<400> SEQUENCE: 6
ggatcccgtt agaagttttc cttgttgaaa                                    30

<210> SEQ ID NO 7
<211> LENGTH: 24
<212> TYPE: DNA
<213> ORGANISM: Artificial Sequence
<220> FEATURE:
<223> OTHER INFORMATION: GAPDH forward primer

<400> SEQUENCE: 7
tccatgacaa ctttggcatc gtgg                                          24

<210> SEQ ID NO 8
<211> LENGTH: 24
<212> TYPE: DNA
<213> ORGANISM: Artificial Sequence
<220> FEATURE:
<223> OTHER INFORMATION: GAPDH reverse primer

<400> SEQUENCE: 8
gttgctgttg aagtcacagg agac                                          24
```